United States Patent [19]

Heider et al.

[11] Patent Number: 5,783,697

[45] Date of Patent: Jul. 21, 1998

[54] PREPARATION OF VINYL CARBAMATES

[75] Inventors: Marc Heider, Neustadt; Jochem Henkelmann, Mannheim; Michael Karcher, Schwetzingen; Thomas Rühl, Frankenthal, all of Germany

[73] Assignee: BASF Aktiengesellschaft, Ludwigshafen, Germany

[21] Appl. No.: 776,107

[22] PCT Filed: Jul. 18, 1995

[86] PCT No.: PCT/EP95/02805

§ 371 Date: Jan. 21, 1997

§ 102(e) Date: Jan. 21, 1997

[87] PCT Pub. No.: WO93/02498

PCT Pub. Date: Feb. 1, 1996

[30] Foreign Application Priority Data

Jul. 20, 1994 [DE] Germany ............... 44 25 677.9

[51] Int. Cl.$^6$ ............... C07D 295/205; C07D 211/06; C07C 269/04
[52] U.S. Cl. ............... 544/172; 544/389; 546/245; 560/24; 560/25; 560/27; 560/28; 560/157; 560/158
[58] Field of Search ............... 544/172, 389; 546/245; 560/24, 25, 27, 28, 158, 157

[56] References Cited

U.S. PATENT DOCUMENTS 2,377,085  5/1945  Kung ............... 260/463

OTHER PUBLICATIONS

Mahe, Roger et al. "Catalytic Synthesis of Vinyl Carbamates from Carbon Dioxide and Alkynes with Ruthenium Complexes," J. Org. Chem. 1989, 54, 1518–1523, Mar. 1989.
Olofson et al., *Tetrahedron Letters*, No. 18, pp. 1563–1566, 1977.
Olofson et al., *J. Org. Chem.*, vol. 43, No. 4, 1978.
Lee, *J. Org. Chem.*, vol. 30, pp. 3943–3945, 1965.
Mahe et al., *J. Org. Chem.* vol. 54, pp. 1518–1523, 1989.
*Chem. Abst.*, vol. 114, No. 20, AN 186109t (1991).

*Primary Examiner*—Michael G. Ambrose
*Attorney, Agent, or Firm*—Keil & Weinkauf

[57] ABSTRACT

Vinyl carbamate compounds are prepared by reacting appropriate secondary amines with carbon dioxide and acetylenically unsaturated compounds in the presence of a compound of a metal from the platinum group, in particular a ruthenium compound, with either one of the two process steps (a) and (b) or, preferably, both being carried out:

(a) the acetylene compound is reinjected during the reaction;

(b) the reaction is carried out in the presence of a tertiary amine.

14 Claims, No Drawings

PREPARATION OF VINYL CARBAMATES

This application is a national stage filing under 35 USC 371 and was based upon PCT International Application No. PCT/EP95/02805, which was filed Jul. 18, 1995.

The present invention relates to a process for preparing vinyl esters of carbamic acid compounds. In particular, the present invention relates to a process for preparing compounds of this type, in which the reaction of secondary amines with carbon dioxide and acetylene compounds is carried out in the presence of catalysts from the group of platinum metals.

The preparation of vinyl carbamates from vinyl chloroformate and amines is a reaction which has been described in detail (R. A. Olofson et al.; THL 18, 1563–1566 (1977)).

Two variants are known for the preparation of vinyl chloroformate starting from carbon oxychloride. On the one hand reaction with mercury enolate (R. A. Olofson et at.; JOC, 43, 752, (1978)), and on the other hand reaction with ethylene glycol to give ethylene glycol bischloroformate which is subsequently cleaved thermally to vinyl chloroformate (L. H. Lee, JOC 30, 3943, (1965); U.S. Pat. No. 2,377,095).

Besides the great safety precautions necessary when working with carbon oxychloride, there is a highly toxic risk in the use of organomercury compounds.

Thermal elimination on ethylene glycol bischloroformate takes place only with poor selectivity and the formation of toxicologically objectionable byproducts.

P. H. Dixneuf has described a synthesis of vinyl carbamates from secondary amines, carbon dioxide and acetylene (J. Org. Chem. 54, 1518 (1989)). This entailed acetylene being dissolved in a solvent at −50° C. and reacted in an autoclave with carbon dioxide and a secondary amine with catalysis by ruthenium trichloride at 80° C. to give the vinyl carbamate. The yields in this process are moderate.

J. of Organic Chemistry, Vol. 54, No. 7, p. 1518 (1989) relates to a process for preparing vinyl carbamates by reacting secondary amine with carbon dioxide and acetylene, vinylacetylene or hexyne, with vinyl carbamates being obtained in the presence of ruthenium compounds with or without catalytic amounts of a free phosphine.

It is an object of the present invention to improve the process as known from the prior art in such a way that high yields and/or high selectivity, preferably both, is achieved.

We have found that this object is achieved by a process for preparing vinyl carbamate compounds. These compounds have the formulae (I) and (II)

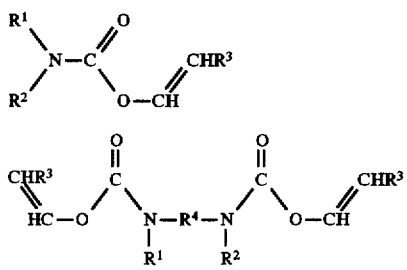

where

R$^1$ and R$^2$ each monovalent hydrocarbon radicals with 1 to 6 carbon atoms, in particular alkyl or aryl- and/or cycloalkyl-substituted alkyl with 1 to 6 carbon atoms, aryl or alkyl- and/or cycloalkyl-substituted aryl with 6 to 10 carbon atoms and cycloalkyl or alkyl- and/or aryl-substituted cycloalkyl with 3 to 10 carbon atoms, or R$^1$ and R$^2$ form, together with the nitrogen to which they are bonded, a heterocyclic group with 5 to 7 ring members and 1 to 3 hetero atoms from the group of O, N, S.

R$^3$ is alkyl or aralkyl with 1 to 6 carbon atoms, cycloalkyl with 3 to 10 carbon atoms, aryl or alkaryl with 6 to 10 carbon atoms, R$^4$ is a divalent hydrocarbon radical with 1 to 10 carbon atoms, in particular alkylene or aryl- and/or cycloalkyl-substituted alkylene with 1 to 6 carbon atoms, arylene or alkyl- and/or cycloalkyl-substituted arylene with 6 to 10 carbon atoms and cycloalkylene or alkyl- and/or aryl-substituted cycloalkylene with 3 to 10 carbon atoms, or R$^4$ and R$^1$ and/or R$^4$ and R$^2$ or R$^4$ and R$^2$ and R$^1$ form, with the particular nitrogen atoms to which they are bonded, a heterocyclic group with 5 to 7 ring members and 1 to 3 hetero atoms from the group of O, N, S.

In the process, the appropriate secondary amines of the formulae (III) and (IV)

where R$^1$, R$^2$, R$^3$ and R$^4$ have the abovementioned meanings, are reacted with carbon dioxide and acetylenically unsaturated compounds of the formula (V)

where R$^3$ has the abovementioned meaning. This reaction takes place in the presence of a compound of a metal from the platinum group, in particular a ruthenium compound.

In this reaction, according to the invention process step (b) with or without process step (a), or, preferably both, are carried out:

(a) the acetylene compound is reinjected during the reaction;

(b) the reaction is carried out in the presence of a tertiary amine.

It has been found, surprisingly, that secondary amines can be reacted with carbon dioxide and acetylene to give the vinyl carbamates in distinctly higher yields when there is continuous reinjection of acetylene during the reaction and a tertiary amine is added to the reaction.

Amine Compounds

Particularly suitable amine compounds of the formulae (III) and (IV) are piperidine compounds morpholine compounds piperazine compounds dialkylamine compounds with 2 to 20 carbon atoms.

Preferred amine compounds are piperidine, N-ethylpiperidine, morpholine or diethylamine.

Acetylene Compounds

Preferred examples of the acetylene compounds which can be employed according to the invention are acetylene
propyne
1-butyne
1-hexyne
phenylacetylene
vinylacetylene
diacetylene

Catalysts

Catalysts which can be employed are compounds of the platinum metals in all oxidation states, preferably compounds of ruthenium and of palladium as such, eg. $RuCl_3$, $Ru(acac)_3$, $Ru_3(CO)_{12}$ or $PdCl_2$. Various complexing agents can be employed for the compounds of the metals of the platinum group. Preferred are aliphatic and aromatic phosphines, phosphites and amines (eg. tributylphosphine, tripheniylphosphine, trimethyl phosphite, triethylamine). It is also possible according to the invention to use multidentate ligands such as 1,2-bis(dimethylphosphino)ethane or tetramethylethylenediamine (TMEDA).

The platinum metal compound is employed in amounts of from 0.1 to 4 mol %, preferably from 0.5 to 2 mol %, based on amine group employed. The complexing agent is preferably employed in 0.5 to 4 times the molar amount based on platinum metal compound employed.

Preferred Operating Conditions

The reaction is carried out at from 50° to 200° C., in particular from 80° to 120° C. The pressure in the reaction is from 1 to 50 bar. The reaction takes from 1 to 12 hours.

It is particularly advantageous first to react carbon dioxide with the amine and only then to add the acetylene compound to the reaction.

The amine can be employed as such, if it is liquid, or else as solution in various organic solvents such as toluene, tetrahydrofuran or acetonitrile.

Tertiary Amines

The tertiary amines employed according to the invention preferably have 3 to 30 carbon atoms in the hydrocarbon radicals. Examples of tertiary amines which can be employed are triethylamine
4-dimethylaminopyridine
DABCO (diazabicyclooctane)
1,8-bis(dimethylamino)naphthalene
trioctylamine.

Triethylamine is currently preferred.

The tertiary amines are employed in catalytic to stoichiometric amounts for this purpose, with stoichiometric amounts being based on the secondary amino groups in the compounds of the formula (III) or (IV) employed.

Isolation of the Vinyl Carbamate Compounds

The vinyl carbamate compounds formed in the process according to the invention are isolated from the reaction mixture preferably by simple distillation of the crude vinylation product.

Preferred embodiments of the invention are indicated in the dependent claims and in the following examples.

EXAMPLE 1

75 g of piperidine and 1.5 g of ruthenium trichloride hydrate were added to 75 g of acetonitrile and, at room temperature, 10 bar of carbon dioxide were injected to constant pressure. The mixture was then heated to 100° C. and acetylene was subsequently injected, up to a total pressure of 20 bar, until the pressure was constant.

The reaction mixture was subsequently washed with aqueous hydrochloric acid, the acetonitrile was removed, and distillation was carried out.

The yield (mol % from secondary amine employed) of vinyl N-piperidinecarboxylate was 63% of theory.

EXAMPLE 2

Morpholine was reacted with carbon dioxide and acetylene as in Example 1. The yield of vinyl N-morpholinecarboxylate after workup and distillation was 49% of theory.

EXAMPLE 3

N-Ethylpiperazine was reacted with carbon dioxide and acetylene as in Example 1. After removal of the acetonitrile, the product was distilled. The yield of vinyl N-ethyl-N'-piperazinecarboxylate was 93% of theory.

EXAMPLE 4

Diethylamine was reacted with carbon dioxide and acetylene as in Example 1. The yield of vinyl N,N-diethylcarbamate after removal of the acetonitrile and distillation was 10% of theory.

EXAMPLE 5

Diethylamine was reacted in acetonitrile and 30 ml of triethylamine with carbon dioxide and acetylene as in Example 1. The yield of vinyl N,N-diethylcarbamate after workup and distillation was 75% of theory.

We claim:

1. A process for preparing a vinyl carbamate compound of the formula (I) or (II)

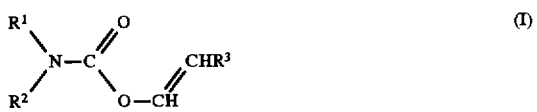

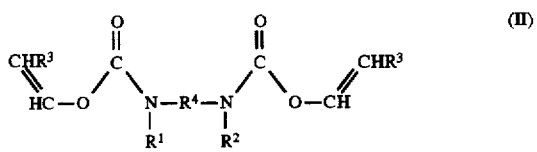

where each of $R^1$ and $R^2$ are monovalent hydrocarbon radicals having 1 to 6 carbon atoms; or $R^1$ and $R^2$, together with the nitrogen to which they are bonded, form a heterocyclic group with 5 to 7 ring members and from 1 to 3 hetero atoms selected from O, N and S;

$R^3$ is alkyl with 1 to 6 carbon atoms; cycloalkyl with 3 to 10 carbon atoms; aryl or alkaryl with 6 to 10 carbon atoms;

$R^4$ is a divalent hydrocarbon radical with 1 to 10 carbon atoms; or $R^1$ and $R^4$, $R^2$ and $R^4$, and $R^1$ and $R^2$, together with the nitrogen atom to which they are bonded, form a heterocyclic group with from 5 to 7 ring members and from 1 to 3 hetero atoms selected from O, N and S;

said process comprising reacting a secondary amine of the formula (III) or (IV)

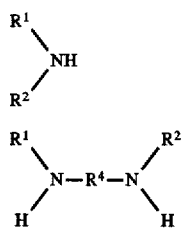

with carbon dioxide and an acetylenically unsaturated compound of the formula (V)

where $R^3$ has the above mentioned meanings;

said reaction being carried out in the presence of a compound of a metal from the platinum group; said reaction being carried out in the presence of a tertiary amine; and wherein the acetylene compound is reinjected during the reaction.

2. A process as defined in claim 1, wherein the reaction is carried out at a temperature of from 50° to 200° C., a pressure of from 1 to 50 bar, and for a duration of from 1 to 12 hours.

3. A process as defined in claim 1, wherein the reaction of the amine with carbon dioxide and acetylene is carried out in the presence of $Ru^{III}$ compounds.

4. A process as defined in claim 3, wherein the reaction of the amine with carbon dioxide and acetylene compound is carried out in the presence of ruthenium trichloride as catalyst.

5. A process as defined in claim 1, wherein the reaction of the amine with carbon dioxide and acetylene compound is carried out in the presence of compounds of the platinum metals with the addition of complexing agents selected from phosphines, phosphites and amines.

6. A process as defined in claim 1, wherein a piperidine compound, a morpholine compound, a piperazine compound or a dialkylamine compound, is used as compound of the formula (III).

7. A process as defined in claim 1, further comprising adding a solvent to the reaction mixture, said solvent being selected from the group consisting of toluene, tetrahydrofuran, dimethyl sulfoxide, acetonitrile and N-methylpyrrolidone.

8. A process as defined in claim 1, wherein an excess of acetylene compound of from 1.5 mol to 10 mol of acetylene compound based on 1 mol of the secondary amine is used.

9. A process as defined in claim 1, wherein acetylene ($R^3$=H) is used as acetylene compound.

10. A process as defined in claim 1, wherein triethylamine is used as tertiary amine.

11. A process as defined in claim 1, wherein the secondary amine compound is first reacted with carbon dioxide and subsequently the acetylene compound is added.

12. A process as defined in claim 1, wherein the metal compound from the platinum group is a ruthenium compound.

13. A process as defined in claim 11, wherein from 1 to 2 mol of carbon dioxide are reacted with the secondary amine under a pressure of about 50 bar of carbon dioxide, and wherein 1 to 10 mol of the acetylenically unsaturated compound are used, and the reaction, following the addition of the ethylene compound, is allowed to proceed for from 2 to 12 hours.

14. A process as defined in claim 6, wherein the compound of formula (III) is piperidine, morpholine or diethylamine.

* * * * *

UNITED STATES PATENT AND TRADEMARK OFFICE
CERTIFICATE OF CORRECTION

PATENT NO.: 5,783,697

DATED: July 21, 1998

INVENTOR(S): HEIDER et al.

It is certified that error appears in the above-identified patent and that said Letters Patent is hereby corrected as shown below:

On the cover page, item [87], "WO 93/02498" should be --WO 96/02498--.

Col. 5, claim 1, line 14, formula V should be --$R^3$-C≡CH--.

Signed and Sealed this

Twenty-ninth Day of September, 1998

Attest:

BRUCE LEHMAN

*Attesting Officer*     *Commissioner of Patents and Trademarks*